United States Patent
Mouk et al.

[11] Patent Number: 5,559,278
[45] Date of Patent: * Sep. 24, 1996

[54] METHODS FOR THE DESTRUCTION OF OZONE DEPLETING SUBSTANCES

[75] Inventors: Robert W. Mouk, Westerville; Albert E. Abel, Powell, both of Ohio

[73] Assignee: Commodore Laboratories, Inc., Columbus, Ohio

[*] Notice: The portion of the term of this patent subsequent to Mar. 7, 2014, has been disclaimed.

[21] Appl. No.: 360,398

[22] Filed: Dec. 21, 1994

Related U.S. Application Data

[63] Continuation-in-part of Ser. No. 207,289, Mar. 7, 1994, Pat. No. 5,414,200.

[51] Int. Cl.$^6$ ......................................................... A63D 3/00
[52] U.S. Cl. ............................ 588/205; 570/262; 588/207
[58] Field of Search .............................. 588/205, 207; 423/DIG. 20; 570/262

[56] References Cited

U.S. PATENT DOCUMENTS

| | | | |
|---|---|---|---|
| 2,691,052 | 10/1954 | Cines | 260/648 |
| 3,004,075 | 10/1961 | Marcali | 260/648 |
| 4,436,641 | 3/1984 | Stelz et al. | 252/68 |
| 5,110,364 | 5/1992 | Mazur et al. | 134/2 |
| 5,307,641 | 5/1994 | Kooy | 62/59 |
| 5,414,200 | 5/1995 | Mouk et al. | 588/205 |

FOREIGN PATENT DOCUMENTS

| 59-10329 | 1/1984 | Japan | B01D 53/94 |
|---|---|---|---|

OTHER PUBLICATIONS

Ralph C. Downing, Fluoro Carbon Refrigeration Handbook Prentice Hall, pp. 177, 182–185, 302–303, 306–308 (1988).

*Primary Examiner*—Gary P. Straub
*Attorney, Agent, or Firm*—Howard M. Ellis

[57] ABSTRACT

Ozone depleting fluorocarbon compounds are dehalogenated through more economic reduction reaction with solvated electrons formed from lower equivalents of reactive metals than previously used by reacting the partial reduction products with non-aqueous liquid nitrogen-containing bases, such as ammonia, or alternatively, without any reactive metal by reacting with the base alone. Mixtures of fluorocarbon refrigerants including difficult to separate azeotropes of dichlorodifluoromethane contaminated with chlorodifluoromethane are reclaimed by treating only with weak non-aqueous nitrogen-containing bases to provide essentially chemically pure dichlorodifluoromethane refrigerant suitable for recycling/reuse.

21 Claims, No Drawings

METHODS FOR THE DESTRUCTION OF OZONE DEPLETING SUBSTANCES

CROSS-REFERENCE TO RELATED APPLICATION

This application is a continuation-in-part of application Ser. No. 08/207,289, filed Mar. 7, 1994, now U.S. Pat. No. 5,414,200.

TECHNICAL FIELD

The present invention relates generally to methods of treating ozone depleting substances, and more specifically, to methods of decomposing and purifying chlorofluorocarbon (CFC) refrigerants.

BACKGROUND OF THE INVENTION

Chlorofluorocarbons (CFCs) are synthetic chemical compounds widely used in refrigeration and air conditioning; as aerosol propellants and solvents; in forming foams, including those used in fast-food packaging; and in rigid insulation. Scientists now view these synthetic chemicals as the main threat to Earth's protective ozone layer. Because CFCs are immune to destruction in the troposphere, and because they eventually float upwardly, their manufacture and release have lead to the accumulation of large amounts in the stratosphere. In the stratosphere, CFCs are broken down by sunlight into chlorine, which has a catalytic and destructive effect on ozone. The result has been a significant decline in the global ozone shield and an increase in the amount of harmful ultraviolet radiation reaching the surface of Earth. According to a United Nations' study, every 1 percent drop in ozone will lead to a 3 percent increase in non-melanoma skin cancers in light-skinned people, as well as dramatic increases in cataracts, lethal melanoma cancers, and damage to the human immune system. Higher levels of UV light may also worsen ground-level pollution and hurt plants, animals, and especially light sensitive aquatic organisms.

As a result, destruction of CFCs, and in some instances, reclamation of CFC refrigerants is a vital component of the national and global strategies for protection of the earth's ozone layer in a manner consistent with minimal economic disruptions associated with the phase-out of this class of chemicals. There are still sizable reserves of CFCs on hand which must be treated and converted to environmentally benign substances. Likewise, until existing refrigeration and air conditioning equipment is replaced or retrofitted with devices which are capable of operating with more environmentally friendly refrigerants, as CFC production is curtailed and eventually eliminated, industry and consumers must rely increasingly on the availability of reclaimed refrigerants.

Various methods have been proposed for the destruction of unwanted CFCs, such as thermal oxidation, catalytic decomposition, supercritical water oxidation, plasma destruction methods, biological processes, UV photolysis, to name but a few. Many are either in experimental stages of development, economically unattractive or incapable of selectively decomposing only specifically targeted compounds.

One other method for the destruction of CFCs is disclosed in U.S. Pat. No. 5,110,364 by Mazur et al, which provides for chemically degrading unwanted CFCs by dehalogenation reactions through solvated electron chemistry. Mazur et al disclose the formation of solvated electrons through dissolving metal reactions with nitrogen-containing bases, such as ammonia wherein at least one chlorine atom of the CFC compound is removed during the reaction to yield products having reduced environmental impact. A somewhat related process is also described in Japanese unexamined application 59-10329 (1984) to Showa Denko KK. Contrary to the disclosures of the earlier Showa Denko process, Mazur et al discovered the reduction of CFCs or other chlorinated organics, e.g. PCBs, with solvated electrons could be successfully carried out in the presence of substances previously thought to interfere with the stability of the solvated electrons or selectivity of the reaction. Mazur et al discovered the need for removing previously considered competing substances, such as oxygen, carbon dioxide, water, etc., from the reaction mixture was not required, and such costly pretreatment step(s) could be omitted.

While solvated electrons provide a practical solution for disposing of fluorocarbon compounds, including CFCs, in practice metal consumption and solvent requirements, e.g. sodium and ammonia are significant cost elements. Together, the two can make up as much as 70 percent of total operating costs. Of the two main reactants, ammonia is the far less costly, and processes for ammonia recovery are available. However, metals such as calcium, sodium and potassium are non-recoverable, and more costly consumable reactants which can detract from economics of the process.

Accordingly, it would be highly desirable to have an improved more economic process for the dehalogenation and destruction of fluorocarbons, and particularly CFCs, which process also allows for purification of contaminated refrigerant compositions. It would also be desirable to have as an improvement in the reclamation of such compounds a significant reduction over the usual stoichiometric equivalents of metal reactant to refrigerant normally employed to dehalogenate targeted compounds, and in some instances, metal requirements entirely eliminated from the process.

SUMMARY OF THE INVENTION

The term "refrigerant" as used throughout the specification and claims is a generic term intended to mean fluorocarbon compounds as a class of chemicals which are suitable for use in refrigeration and air conditioning equipment, but may have other applications. The term thus embraces halofluorocarbons and halofluorohydrocarbons, such as chlorofluorocarbons (CFCs), bromofluorocarbons, chlorofluorohydrocarbons, and so on. Likewise, the term "refrigerant" is also intended to include fluorocarbons which are useful as solvents, aerosol propellants, in manufacturing synthetic foams, packaging, insulation, retardant compounds for fire extinguishers, and the like. Thus, it should be understood the term "refrigerant" is intended to embrace a broader range of compounds then merely those which are suitable for air conditioning and refrigeration applications. They include products commercially available under trademarks, such as Freon, Halon, Frigen, Arcton, Genetron and Isotron.

In accordance with the invention an improved method is provided for dehalogenating refrigerants, and more particularly, fluorohydrocarbon refrigerants where instead of relying on the dissolution of a reactive metal in liquid ammonia or other nitrogen-containing base in the formation of solvated electrons, the improved method relies on the steps of:

(a) providing a fluoroalkane refrigerant having at least one hydrogen atom and at least one other halogen atom in addition to fluorine, and (b) in the absence of a dissolved metal reactant reacting the fluoroalkane refrigerant with only the nitrogen-containing base to dehalogenate and decompose the refrigerant. The nitrogen-containing base is non-aqueous.

Fluoroalkane as recited herein is intended to include halofluorohydrocarbons having in addition at least one hydrogen atom, at least one other halogen atom in addition to fluorine, i.e., chlorine, bromine and/or iodine. Fluoroalkane refrigerants are preferably intended to embrace halofluorohydrocarbons with <4 carbon atoms, and more preferably, compounds having 1 or 2 carbon atoms.

Unlike the foregoing method, U.S. Pat. No. 2,738,371 (Parmelee) provides for treating perfluorocarbons, i.e., compounds composed exclusively of 5 to 25 carbon atoms which are fully substituted with fluorine. Parmelee found that in the synthesis of perfluorocarbons, impurities develop consisting of incompletely fluorinated compounds containing up to 0.1 percent hydrogen. In reacting the impure perfluorocarbon composition with ammonia or an amine according to Parmelee's methods the fluorohydrocarbon is converted to fluorocarbon amine compounds.

In contrast, experimentation by the present inventors has shown that weak non-aqueous nitrogen-containing bases, like ammonia are capable of fully reacting with ozone depleting halofluorohydrocarbons, and particularly chlorofluorohydrocarbons having 1 or 2 carbon atoms, such as chlorodifluoromethane to selectively dehalogenate and decompose them. Advantageously, it was also found that the environmentally harmful halofluorohydrocarbons can be eliminated without introducing metal into the reaction. In addition to more attractive economics of the process, any potential hazards associated with handling, transporting and storage of highly reactive alkali metals are avoided.

It is yet a further object of the invention to selectively dehalogenate compositions having a plurality of refrigerant compounds. Accordingly, the invention also contemplates reclamation methods wherein halofluorocarbon refrigerants which have become contaminated with halofluorohydrocarbon compounds are effectively purified. The method is carried out by the steps of:

(a) providing a composition with at least two refrigerants, (i) a primary perhalogenated compound and (ii) a contaminating fluoroalkane compound having at least one hydrogen atom and at least one other halogen atom in addition to fluorine;

(b) reacting the refrigerant composition of step (a) with a weak base, namely a non-aqueous nitrogen-containing compound, such as ammonia to selectively decompose the contaminating fluoroalkane refrigerant compound (ii), and (c) recovering a refrigerant composition from the reaction mixture of step (b), the composition comprising the primary perhalogenated refrigerant compound (i). The recovered composition is sufficiently free of the contaminating fluoroalkane refrigerant (ii) to enable recycling/reuse.

More preferably, the process comprises the steps of:

(a) providing a composition having at least two refrigerants, (i) a primary perhalogenated compound, usually a halofluorocarbon, e.g., chlorofluorocarbon, bromofluorocarbon, etc., and (ii) a contaminating fluoroalkane refrigerant compound having one or two carbon atoms, at least one hydrogen atom and at least one other halogen atom in addition to fluorine, e.g., chlorine, bromine or iodine;

(b) reacting the refrigerant composition of step (a) with a non-aqueous nitrogen-containing base to selectively decompose the contaminating fluoroalkane refrigerant compound (ii), and (c) recovering a refrigerant composition from the reaction mixture of step (b), the composition comprising the primary perhalogenated refrigerant compound (i), the recovered composition being sufficiently free of the contaminating fluoroalkane refrigerant compound (ii) to enable recycling/reuse.

This aspect of the invention is particularly unique in view of the discovery that weak nitrogen-containing bases are capable of selectively dehalogenating/decomposing halofluorohydrocarbons (ii) without also reacting with the primary fluorocarbon compounds (i). The selectivity of the process is also significant in permitting the recovery of refrigerants from mixtures which otherwise could not be readily purified through distillation methods because of their forming azeotropes with other refrigerants. Heretofore, such azeotropes were disposed of by decomposing the entire mixture since there was no practical and economic means for separation and recovery of the still useful refrigerant compounds.

It is still a further object of the invention to provide for an improved method of dehalogenating fluorocarbon refrigerants by a reduction mechanism through dissolving metal reaction in a nitrogen-containing base, such as ammonia. Unlike earlier methods for the destruction of unwanted ozone depleting perhalogenated refrigerants with solvated electrons which typically employed 8 equivalents of reactive metal per mole of refrigerant, the present inventors discovered that dehalogenation of such refrigerants could be effectively performed with only a fraction of the metal previously used, thereby making the process economically more attractive. The improved method includes the steps of:

(a) providing a perhalogenated fluorocarbon refrigerant having at least one other halogen atom in addition to fluorine, e.g., chlorine, bromine and iodine;

(b) forming a solution of solvated electrons by dissolving in ammonia or other weak nitrogen-containing base a substoichiometric amount of the reactive metal in an amount about sufficient to partially reduce the perhalogenated refrigerant of step (a) by removing one halogen atom therefrom;

(c) reacting the refrigerant of step (a) in the solution of solvated electrons of step (b), the reaction being conducted at temperatures sufficiently low as to retard reactions of the solvated electrons and liquid ammonia or other nitrogen-containing base with by-products of the reduction reaction, and (d) elevating the temperature of the reaction mixture of step (c) to initiate further dehalogenation by reacting with the ammonia or other nitrogen-containing base to form compounds which are non-ozone depleting.

The foregoing method is preferably performed by the steps of:

(a) providing a perhalogenated fluorocarbon refrigerant;

(b) forming a solution of solvated electrons by dissolving in the liquid ammonia or other nitrogen-containing base the reactive metal in an amount about sufficient to partially reduce the perhalogenated fluorocarbon refrigerant of step a;

(c) reacting the refrigerant of step (a) in the solution of solvated electrons of step (b), the reaction being conducted at temperatures sufficiently low as to retard reactions of the solvated electrons and liquid ammonia or other nitrogen-containing base with by-products of this reduction reaction, and (d) elevating the temperature of the reaction mixture of step (c) to initiate further dehalogenation by reacting with the liquid ammonia or other nitrogen-containing base.

DESCRIPTION OF THE PREFERRED EMBODIMENTS

Methods of the invention include the dehalogenation and destruction of "fluoroalkane" refrigerants which term for purposes of this invention is intended to mean principally fluoromethane type refrigerants, but also fluoroethane types. The fluoroalkane refrigerants have at least one hydrogen atom and one other halogen atom in addition to fluorine, namely chlorine, bromine and/or iodine. Representative fluoroalkane types include refrigerants available under the E.I. dupont trademark Freon®, such as Freon 22 (chlorodifluoromethane), Freon 21 (fluorodichloromethane), Freon 31 (chlorofluoromethane), Freon 31B1 (bromofluoromethane), Freon 22B1 (bromodifluoromethane), and mixtures of the same. Other fluoroalkane refrigerants include, for instance, 1,1,2,2-tetrachloro-2-fluoroethane (FC-121); 1,1,1-trifluoro-2,2-dichloroethane (FC-123).

One preferred embodiment of the invention includes reacting the foregoing fluoroalkane refrigerants with a non-aqueous nitrogen-containing base. The expression "non-aqueous nitrogen-containing base", or similar variations thereof as appearing in the specification and claims is intended to mean substantially free of water. That is to say, the expression is intended to denote anhydrous bases which are free of any water, but also nitrogen-containing bases having small or minor amounts of water ranging from 3 percent or less, which may be present, for example, as an impurity.

Representative examples of non-aqueous nitrogen-containing bases include mainly ammonia, i.e. anhydrous liquid ammonia and liquid ammonia having minor amounts of water, i.e. 3 percent or less. Other suitable non-aqueous nitrogen-containing bases in addition to ammonia which may be employed in the dehalogenation of fluoroalkane refrigerants include primary amines, secondary amines, tertiary amines, cyclic amines, heterocyclic alkyl mono and polyamines and mixtures thereof. Representative examples of such bases include methyl amine, ethyl amine, dimethyl amine, diethyl amine, triethyl amine, n-propyl amine, piperidine, morpholine and ethylenediamine.

The foregoing nitrogen-containing bases are weak bases. For purposes of this invention the expression "weak base" is generally intended to encompass mainly nitrogen-containing bases having a $pK_b$ in the range of 2 to 5.

The non-aqueous nitrogen-containing bases are suitable for use as is, or they may be mixed with other organic solvents provided the solvents are substantially soluble in the refrigerant, and do not react with the base. Representative examples of suitable organic solvents include primary alcohols, such as methanol, ethanol, propanol, butanol; secondary alcohols like 2-propanol; ethers, such as diethyl ether and 1,4-dioxane; glycol monoethers like methoxyethanol and butoxypropanol; nitriles, such as acetonitrile, and amides like N,N-dimethylformamide or N,N-dimethylacetamide.

Dehalogenation of fluoroalkanes with non-aqueous nitrogen-containing bases is readily performed in a pressure vessel at ambient temperature conditions, which includes temperatures generally in the range of about 10° to about 70° C. The concentration of the nitrogen-containing base employed is generally in the range of about 10 percent to about 100 percent. The reactions are preferably conducted under anaerobic conditions. A means of removing insoluble reaction products (salts) by filtration is provided.

As a further preferred embodiment, the invention includes methods for selective dehalogenation of refrigerant compositions containing two or more refrigerants. More particularly, the invention includes methods for purification of refrigerant compositions containing useful primary refrigerants which have become contaminated with other refrigerants. Expressions like "primary refrigerant" and "primary perhalogenated refrigerant" as appearing herein are used to denote the specific refrigerant(s) desired for recovery from contaminated refrigerant mixtures in the dehalogenation process. Primary refrigerants include mainly refrigerants which are perhalogenated, or in other words, fluorocarbon refrigerants in which all the carbons are fully substituted with halogen atoms. They include such representative examples as Freon® 11 (fluorotrichloromethane), Freon 12 (dichlorodifluoromethane), Freon 13 (chlorotrifluoromethane), Freon 14 (tetrafluoromethane), Freon 13B1 (bromotrifluoromethane), and so on.

The expression "other refrigerant" is used herein to denote the contaminating or unwanted refrigerant portion to be eliminated from refrigerant compositions containing the primary refrigerant. Other refrigerants correspond to the "fluoroalkane refrigerants" previously discussed in connection with the first embodiment of the invention, and includes halofluorohydrocarbon compounds having <4 carbons, and more preferably 1 or 2 carbon atoms, at least one hydrogen atom and at least one other halogen atom in addition to fluorine, e.g. chlorine, bromine and/or iodine. Representative examples include chlorodifluoromethane, fluorodichloromethane, chlorofluoromethane, bromofluoromethane, bromodifluoromethane, and mixtures of the same.

This second embodiment of the invention is useful in reclaiming refrigerant compositions. In order to qualify for reuse, reclaimed refrigerants are required to meet the American Refrigeration Institute's "700" specifications which stipulate the permissible levels of contaminants. That is, strict limits are placed on moisture, particulates, acidity, oil content, non-condensible gases, and other refrigerants present. Existing reclamation processes are capable of meeting all of the foregoing criteria with the exception of "other refrigerants", which are not permitted to exceed 0.5 percent maximum.

Hence, the second embodiment of the invention is useful in treating mixtures of fluorocarbon compounds, including those contaminated with >0.5 percent of other refrigerant. However, methods of the present invention are also effective in treating compositions containing minor or even trace amounts, i.e., <0.5 percent other refrigerant(s). One representative example of a widely found refrigerant mixture is dichlorodifluoromethane also known as Freon® 12 or FC-12, which is frequently contaminated with Freon 22 or chlorodifluoromethane, both hereinafter called R-12 and R-22, respectively. Although removal of the unwanted R-22 contaminant from such a mixture would appear to be readily accomplished by distillation due to differences in their boiling points (R- 12 b.p. −29.8° C. and R-22 b.p. −41° C.), separation by distillation is not readily achieved due to the formation of an azeotrope consisting of 75 percent R-22, when the two refrigerants become mixed.

The principal object of this embodiment of the invention is the selective chemical decomposition of other refrigerants in compositions of refrigerant mixtures without loss of the primary refrigerant. This includes the steps of separation and recovery of the composition containing the primary refrigerant from the reaction medium in a refined or purified state free or virtually free of other refrigerant, so as to meet ARI specifications for other refrigerants. The methods of this second embodiment are especially useful in recycling discontinued or potentially scarce refrigerant compounds.

While the methods of the invention are especially useful in the reclamation of contaminated perhalomethane type primary refrigerants the invention contemplates the purification and recovery of other perhaloalkane primary refrigerants as well, such as the fluoroethanes and fluorobutanes. Representative examples include fluorocarbon or FC-112 (1,1,2,2-tetrachloro-1,2-difluoroethane), FC-113 (1,1,2-trichloro-1,2,2-trifluoroethane), and the like.

In addition to the reclamation of refrigerant compositions comprising a single perhalogenated primary refrigerant contaminated with other refrigerant(s), the invention contemplates the purification of refrigerant mixtures having similar boiling points, and particularly azeotrope refrigerants, like Freon 500 (dichlorodifluoromethane and 2,2-difluoroethane), Freon-503 (trifluoromethane and chlorotrifluoromethane), and particularly an azeotrope of dichlorodifluoromethane in which the halofluorohydrocarbon, chlorodifluoromethane is the other refrigerant.

The reaction of the non-aqueous nitrogen-containing base with the contaminated refrigerant composition is performed in a closed pressure vessel at ambient temperature conditions. The process may be either batch or continuous. With amines of suitably high boiling point purified refrigerant may be separated from the reaction mixture by evaporation. However, with ammonia or low boiling amines the separation is accomplished by passing the vaporized mixture through water, dilute acid or a sequence of the two to selectively dissolve the amine either as the free base or as a salt thereof. The refrigerant vapors are then compressed and cooled to bring them to a liquid state.

As a third embodiment of the invention, fluorocarbon refrigerants, and particularly perhalogenated types which are not readily dehalogenated with weak bases, such as dichlorodifluoromethane, chlorotrifluoromethane, bromotrifluoromethane, and other perhalogenated fluorocarbons are partially dehalogenated initially through a reduction reaction with solutions of solvated electrons. It was found, this partial dehalogenation reaction of fluorocarbon refrigerants requires as little as one fourth of the reactive metal ordinarily employed in processes, such as disclosed by U.S. Pat. No. 5,110,364 and Japanese Unexamined Application 59-10329 (1984). Such prior methods provide for removal of all halogen atoms from the perhalomethane refrigerants with stoichiometric amounts of reactive metals, such as sodium in the formation of solvated electrons with ammonia or other nitrogen-containing solvent. Unlike earlier methods, the improved process of the immediate invention provides for the removal of as little as a single halogen atom, e.g., chlorine, bromine or iodine, thereby requiring but a fraction of the metal reactant, in view of the lesser requirement for solvated electrons. With the removal of as little as a single halogen atom, further dehalogenation of the fluorocarbon is achieved with the remaining available ammonia or other nitrogen-containing base in the reaction mixture.

While not wishing to be held to any specific mechanism of action relative to this third embodiment, it is nevertheless believed that partial reduction or dehalogenation of a perhalocarbon refrigerant by treating in a solution of solvated electrons might result in hydrogenating the starting refrigerant, and possibly forming an halohydroalkane intermediate which is subject to further dehalogenation through acid-base reaction with the residual ammonia or other nitrogen-containing base remaining in the reaction mixture.

The solvated electrons are formed in a dissolving metal reaction with ammonia or other nitrogen-containing base, such as a fluorocarbon soluble primary amine, secondary amine or tertiary amine. Specific representative examples were previously provided. The reactive metals may consist of alkali metals, such as sodium, potassium and lithium, and alkaline earth metals, like calcium and magnesium. Mixtures of such metals may also be employed. Aluminum may also be used as a dissolving metal. Compared with the stoichiometric amounts of metal per mole of perfluorocarbon refrigerant employed according to earlier methods, the present invention utilizes 2 mole equivalents of reactive metal per mole of perhalogenated fluorocarbon, or in other words, one fourth of the amount of metal previously required.

Reduction of the perfluorocarbon refrigerant with solvated electrons is carried out in a closed pressure vessel at temperatures sufficiently low as to retard reactions which might otherwise occur between by-products of the reduction reaction and the solvated electrons or nitrogen-containing base. Typically, reactions would be conducted at about 0° C. or lower. Subsequently the reaction vessel is allowed to warm to ambient temperature which will in-turn initiate further dehalogenation of the partially dehalogenated fluorocarbon to completely dehalogenate it, i.e. remove the remaining fluorine, chlorine, bromine and/or iodine atoms as an acid-base reaction with residual ammonia or other nitrogen-containing base.

The following specific examples demonstrate the various embodiments of the invention, however, it is to be understood they are for illustrative purposes only and do not purport to be wholly definitive as to conditions and scope.

EXAMPLE I

In order to demonstrate that a nitrogen-containing base, such as ammonia was capable of effectively destroying halohydroalkane refrigerants in the absence of a dissolving metal reactant, such as sodium or calcium, an initial experiment was conducted using a reactor consisting of an Ace Glass, Inc., heavy walled threaded glass tube fitted with a Teflon® stopper and pressure gauge. The tube was charged with 25.0 g of anhydrous liquid ammonia (1.5 moles) and 4.1 g of pure chlorodifluoromethane refrigerant (R-22). The tube was charged while being cooled in dry ice/isopropyl alcohol (IPA). Once charging was completed the tube was sealed and allowed to warm to room temperature. Within 80 minutes after mixing the reactants, salt crystals were observed at the bottom of the tube consisting of by-products of the reaction. Additional salts were observed to be continually forming. Within 140 minutes into the experiment the reaction was judged to be complete and the reactor tube was again cooled in dry ice/IPA to reduce pressure in the tube from the ammonia. The pressure gauge was replaced with a stopper vented through a Teflon tube, and the reaction tube was allowed to warm. When gas evolution ceased 7.5 g of solids were recovered. The stoichiometric yield of products was 8.1 g, indicating at least 93 percent of the R-22 was destroyed in the reaction.

EXAMPLE II

In order to demonstrate the selectivity of weak nitrogen-containing bases in the absence of a dissolving metal, such as potassium or calcium, in the purification of refrigerant mixtures a further experiment was conducted. 90.5 g of a refrigerant mixture consisting of 87.2 percent dichlorodifluoromethane (R-12) and 12.8 percent chlorodifluoromethane (R-22) were charged to a steel tube reactor. The refrigerant charge thus contained 11.6 g (0.13 moles) of R-22. 24.4g or 1.43 moles of anhydrous liquid ammonia were added to the refrigerant mixture. The reactor tube was sealed and allowed to stand for 3 days at ambient temperature conditions. The composition was analyzed, and found to contain 99,754 percent R-12; 0,105 percent R-22, and a trace of other refrigerant (0.141 percent R-32). Analysis showed the reaction to be highly selective in destroying only R-22.

In order to recover substantially pure R-12 from the reaction mixture the ammonia in the reactor is converted to water soluble salts by the addition of dilute aqueous sulfuric acid solution. Because of the insolubility of the R-12 refrigerant in the aqueous salt solution, separate distinct phases form in the reactor consisting of a lower refrigerant phase and an upper aqueous phase. The lower refrigerant phase containing the R-12 can be withdrawn so it is substantially free of the water soluble salts.

EXAMPLE III

To demonstrate the effectiveness of other weak nitrogen-containing bases in dehalogenating halohydroalkanes the experiment of Example I was repeated using ethylenediamine in place of ammonia. Approximately 5.0 g of chlorodifluoromethane was mixed in the glass pressure tube with about 20 ml of ethylenediamine and allowed to warm to room temperature. A vigorous exothermic reaction ensued indicating weak nitrogen-containing bases other than anhydrous liquid ammonia will readily react with halohydroalkane refrigerant.

EXAMPLE IV

Dissolving metal reactions with ammonia or other weak base are useful in the destruction of most refrigerants, including the more stable perhalogenated types. Significantly reduced amounts of dissolving metals then previously required can be effectively used to achieve complete destruction of unwanted refrigerants. This can be shown by charging liquid ammonia to a reaction vessel and allowing it to cool by auto-refrigeration. When a temperature of $-10°$ to $-33°$ C. is reached 2 mol equivalents of calcium metal are added and stirred to give the typical blue solvated electron solution. Eight mole equivalents of dichlorodifluoromethane, about 4 times the amount of refrigerant then metal present to entirely dehalogenate the refrigerant, is allowed to react until the blue color no longer appears. The temperature of the reaction mixture is then allowed to rise. At about room temperature further destruction of the refrigerant occurs through reaction of only the remaining ammonia in the reactor.

While the invention has been described in conjunction with specific examples thereof, they are illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

We claim:

1. A method of purifying a refrigerant composition, which comprises the steps of:
    (a) introducing into a reactor a used refrigerant composition comprising at least two refrigerants, (i) a primary perhalogenated carbon compound having at least one other halogen atom in addition to fluorine and (ii) a contaminating fluoroalkane compound having one or two carbon atoms, at least one hydrogen atom and at least one other halogen atom in addition to fluorine;
    (b) reacting the refrigerant composition of step (a) with a non-aqueous nitrogen-containing base to selectively decompose said contaminating fluoroalkane refrigerant compound (ii), and
    (c) recovering a refrigerant composition from the reaction mixture of step (b), said composition comprising the primary perhalogenated carbon compound (i), said recovered composition being essentially free of the contaminating fluoroalkane refrigerant compound (ii).

2. The method of claim 1 wherein the primary perhalogenated carbon compound (i) of step (a) is a member selected from the group consisting of a chlorofluorocarbon and a bromofluorocarbon.

3. The method of claim 2 wherein the contaminating fluoroalkane refrigerant compound (ii) of step (a) is a chlorofluorohydrocarbon.

4. The method of claim 3 wherein the hydrogen atom on the chlorofluorohydrocarbon of step (a) is on the carbon containing the chlorine atom.

5. The method of claim 1 wherein the hydrogen atom of the contaminating fluoroalkane refrigerant (ii) of step (a) is on the carbon atom containing the other halogen atom in addition to fluorine.

6. The method of claim 1 wherein said non-aqueous nitrogen-containing base is liquid ammonia or a solution comprising liquid ammonia, said solution being substantially soluble in said refrigerant composition.

7. The method of claim 1 wherein said nitrogen-containing base is a member selected from the group consisting of refrigerant soluble primary amines, secondary amines .and tertiary amines.

8. The method of claim 1 wherein said refrigerant composition of step (a) comprises an azeotrope.

9. The method of claim 1 wherein said refrigerant composition of step (a) comprises a mixture of at least two refrigerants having substantially similar boiling points.

10. The method of claim 1 wherein the refrigerant composition of step (a) is an azeotrope comprising dichlorodifluoromethane and chlorodifluoromethane, and the recovered refrigerant composition of step (c) comprises dichlorodifluoromethane.

11. The method of claim 1 wherein the recovered refrigerant composition of step (c) comprises one or more compounds suitable for use in refrigeration or air conditioning equipment.

12. The method of claim 1 including the step of incorporating an organic solvent into the reaction of step (b).

13. The method of claim 1 wherein said nitrogen-containing base is a member selected from the group consisting of methyl amine, ethyl amine, dimethyl amine, diethyl amine, triethyl amine, n-propyl amine, ethylenediamine, piperidine and morpholine.

14. A method of chemically dehalogenating fluorocarbon refrigerants, which comprises the steps of:
    (a) introducing a perhalogenated fluorocarbon refrigerant into a reactor;
    (b) forming a solution of solvated electrons by dissolving in a liquid ammonia or other nitrogen-containing base a reactive metal in an amount about sufficient to only partially dehalogenate the perhalogenated refrigerant by removing at least one of the halogens therefrom;
    (c) reacting the refrigerant of step (a) in the solution of solvated electrons of step (b), said reaction being conducted at temperatures sufficiently low as to minimize reactions of the solvated electrons with by-products of this dehalogenation reaction, and
    (d) elevating the temperature of the reaction mixture of step (c) to initiate further dehalogenation by reacting with the liquid ammonia or other nitrogen-containing base.

15. The method of claim 14 wherein the reactive metal is a member selected from the group consisting of alkali metals, alkaline earth metals, aluminum and mixtures thereof.

16. The method of claim 15 wherein the solution of solvated electrons is formed with about 2 equivalents of reactive metal per mole of perhalogenated fluorocarbon refrigerant present.

17. The method of claim 14 wherein the perhalogenated fluorocarbon refrigerant of step (a) is a chlorofluorocarbon.

18. The method of claim 14 wherein the perhalogenated fluorocarbon refrigerant is a member selected from the group consisting of chlorotrifluoromethane, bromotrifluoromethane, and fluorotrichloromethane.

19. The method of claim 14 wherein the perhalogenated fluorocarbon refrigerant of step (a) is dichlorodifluoromethane.

20. The method of claim 14 wherein less than a stoichiometric amount of metal is employed in step (b) to remove at least one, but fewer than all halogen atoms from the perhalogenated refrigerant.

21. The method of claim 14 wherein said nitrogen-containing base is a member selected from the group consisting of methyl amine, ethyl amine, dimethyl amine, diethyl amine, triethyl amine, n-propyl amine, ethylenediamine, piperidine and morpholine.

* * * * *